United States Patent [19]

Discko, Jr.

[11] Patent Number: 5,122,057
[45] Date of Patent: Jun. 16, 1992

[54] DOSING DENTAL CARTRIDGE

[75] Inventor: John Discko, Jr., Hamden, Conn.

[73] Assignee: Centrix, Inc., Milford, Conn.

[21] Appl. No.: 637,823

[22] Filed: Jan. 7, 1991

[51] Int. Cl.$^5$ .............................................. A61C 5/04
[52] U.S. Cl. ..................................................... 433/90
[58] Field of Search ........................ 433/89, 90, 80, 82

[56] References Cited

U.S. PATENT DOCUMENTS

| | | | |
|---|---|---|---|
| 3,581,399 | 6/1971 | Dragan | 433/90 |
| 3,724,076 | 4/1973 | Schmitz | 433/90 |
| 3,884,231 | 5/1975 | Peters | 128/235 |
| 3,900,954 | 8/1975 | Dragan | 433/90 |
| 4,295,828 | 10/1981 | Rudler | 433/90 |
| 4,391,590 | 7/1983 | Dougherty | 433/90 |
| 4,569,662 | 2/1986 | Dragan | 433/89 |
| 4,708,650 | 11/1987 | Holewinski et al. | 433/90 |
| 4,767,326 | 8/1988 | Bennett et al. | 433/90 |
| 4,784,607 | 11/1988 | Francois | 433/90 |
| 4,863,072 | 9/1989 | Perler | 222/390 |
| 4,963,093 | 10/1990 | Dragan | 433/90 |

FOREIGN PATENT DOCUMENTS 5701465  7/1979  Brazil.

*Primary Examiner*—John J. Wilson
*Assistant Examiner*—Cindy A. Cherichetti
*Attorney, Agent, or Firm*—Paul A. Fattibene; Arthur T. Fattibene

[57] ABSTRACT

A dental cartridge for dispensing a dental material having a body portion made of a material transparent to at least a portion of the visible light spectrum and opaque to the actinic light of the dental material contained therein. Also, a dental cartridge having a body portion formed from a toroidal segment and a coaxial nozzle attached thereto. The dental cartridges are used in a dental syringe for application of the dental material to a patient. Several embodiments provide various discharge end configurations, including hemispherical, conical frustum, and flat. Additionally, dosing indicia are placed on the body portion of the dental cartridge, permitting the dentist to fill the dental cartridge with a predetermined volume of dental material. A specially configured piston having an appendage thereon is used in combination with the dental cartridge for extruding substantially all of the costly dental material therein.

20 Claims, 4 Drawing Sheets

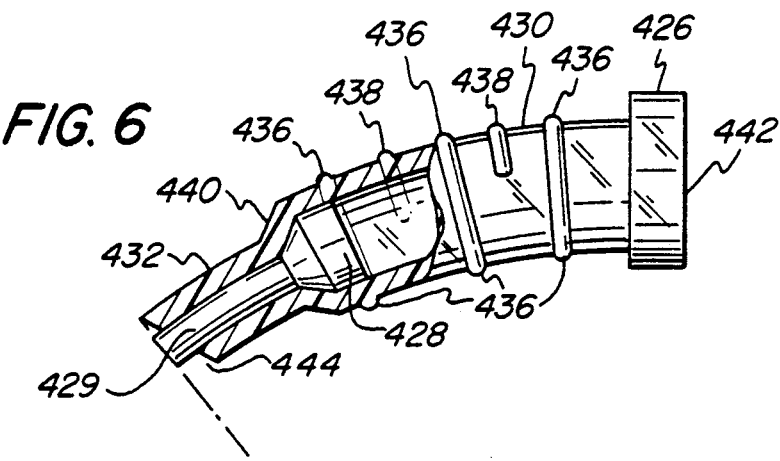
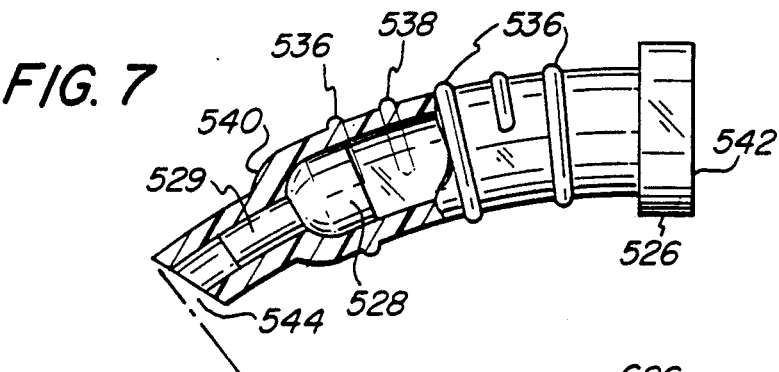
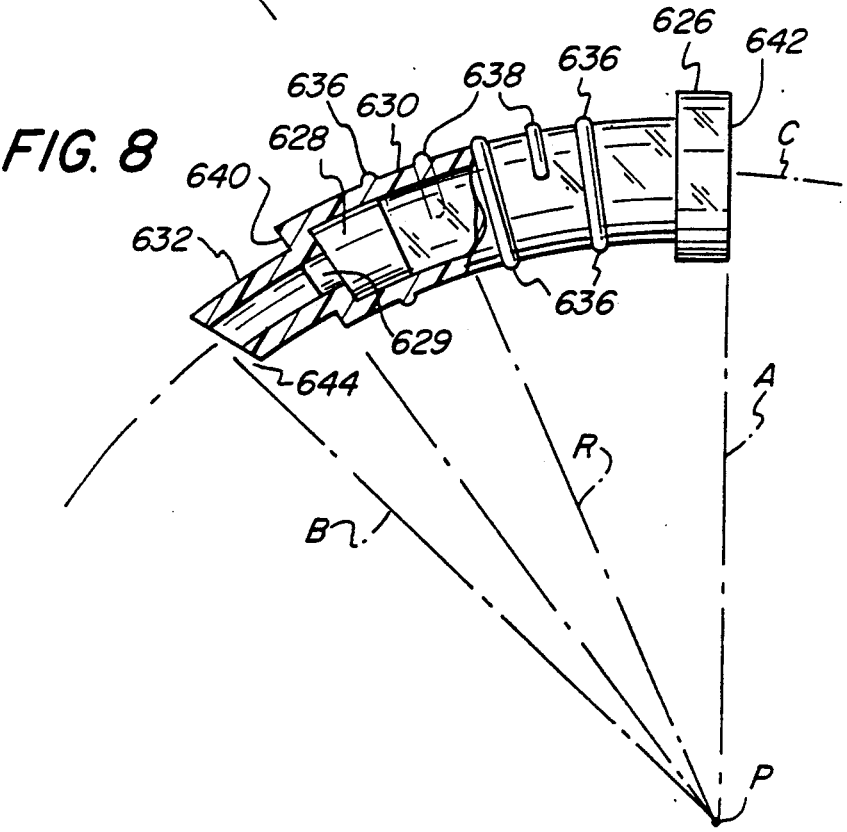

DOSING DENTAL CARTRIDGE

FIELD OF THE INVENTION

The present invention relates generally to dental cartridges for dispensing dental filling composite material with a leveraged extruding syringe and more particularly to an improved cartridge.

BACKGROUND OF THE INVENTION

Since the first introduction of a composite resin dental material filling syringe, such as the one disclosed in U.S. Pat. No. 3,581,399 entitled "Composite Resin Filling Syringe and Technique" issuing to Dragan on Jun. 1, 1971, there have been many improvements thereto. These improvements often related to the cartridge o tip containing the dental filling material used within a syringe, gun, or extruding device.

Two examples of improved dental cartridges can be found in U.S. Pat. No. 4,391,590 entitled "Cartridge for Viscous Material" issuing to Dougherty on Jul. 5, 1983 and U.S. Pat. No. 4,963,093 entitled "Dental Syringe Tip and Syringe Holder Therefor" issuing to Dragan on Oct. 16, 1990. Both of these patents disclose a cartridge or tip to be placed in a syringe for extruding the dental material contained within the cartridge or tip. They both relate to an opaque cartridge having a first linear axis for the reservoir or body portion and a second linear axis for the nozzle discharge portion. Both cartridges are additionally intended to contain a light sensitive dental material that will cure or harden when exposed to a specific wavelength of light. Therefore, the cartridges are intended to be pre-loaded in a controlled environment for subsequent distribution to the dentist. The dentist then dispenses the dental material contained therein in a single application.

While these cartridges or tips are appropriate for some applications, they are not desirable in many others. In many applications, the dentist may wish to fill his own cartridges for dispensing dental material of his own choice. It is often difficult to fill, by hand, an unfilled opaque cartridge. This is because of the inability to see the material being placed therein. Additionally, it is difficult to determine the quantity or volume of material being placed within an opaque cartridge. In many instances, a dentist may not require or desire a full cartridge. Additionally, the straight cartridge having a relatively large end in relation to the nozzle portion makes visibility difficult in the small and confining areas of the mouth where the dentist must work. Also, consistency of material is of primary concern in the application of dental material in a cavity. In the cartridges having multiple axes and a change of direction of material flow, often turbulence or air entrapment can result. This is very undesirable in that voids or inconsistency of material compromises the integrity of the filling. Further, the dental material being relatively expensive, it is undesirable to leave any dental material remaining within the cartridge. The material is often left in the discharge nozzle portion that is at an angle to the body portion.

As should be readily appreciated from the above, there are many instances in which an improved dental cartridge is needed to provide better dental care at a reduced cost.

SUMMARY OF THE INVENTION

The present invention relates to an improved cartridge or tip for dispensing dental material, comprising a body portion opaque to actinic light of the dental material contained therein and transparent to at least a portion of the visible light spectrum. This permits the dentist to see the material being placed within the body portion. In another embodiment, dosing indicia are formed on the body portion so that a dentist, upon filling the cartridge or tip, can place the appropriate volume of material therein.

In another embodiment, the body portion is formed in the shape of a toroidal segment improving visibility and material flow. This embodiment is also combined with a piston having an appendage to fit within the nozzle portion of the cartridge or tip. This permits complete extrusion of the costly dental material.

Accordingly, it is an object of the present invention to permit a dentist to fill a cartridge with a light activated dental material of his own choice.

It is another object of the present invention to avoid wasting costly dental material.

It is yet another object of the present invention to improve the flow characteristics of the cartridge, thereby providing more consistent, less porous fillings.

It is a advantage of the present invention that the dental material is visible within the body portion.

It is another advantage of the present invention that the dental material will not cure within the cartridge.

It is yet another advantage of the present invention that the direction of material flow within the cartridge is not changed.

It is still a further advantage of the present invention that nearly all of the dental material is extruded.

It is a feature of the present invention that the body portion of the cartridge is opaque to actinic light.

It is another feature of the present invention that dosing indicia are placed on the body portion.

It is yet a further feature of the present invention that the nozzle and body portion have a curved common axis, thereby improving flow characteristics.

It is yet a further feature of the present invention that the piston or plug has an appendage adapted to fit the discharge nozzle.

It is still another feature of the present invention that the end of the nozzle has a relief angle.

BRIEF DESCRIPTION OF THE DRAWINGS

FIG. 6 illustrates the toroidal segment embodiment of the present invention.

FIG. 7 illustrates yet another toroidal segment embodiment of the present invention.

FIG. 8 illustrates a still further toroidal segment embodiment of the present invention.

DETAILED DESCRIPTION OF THE PREFERRED EMBODIMENTS

Figure 1:
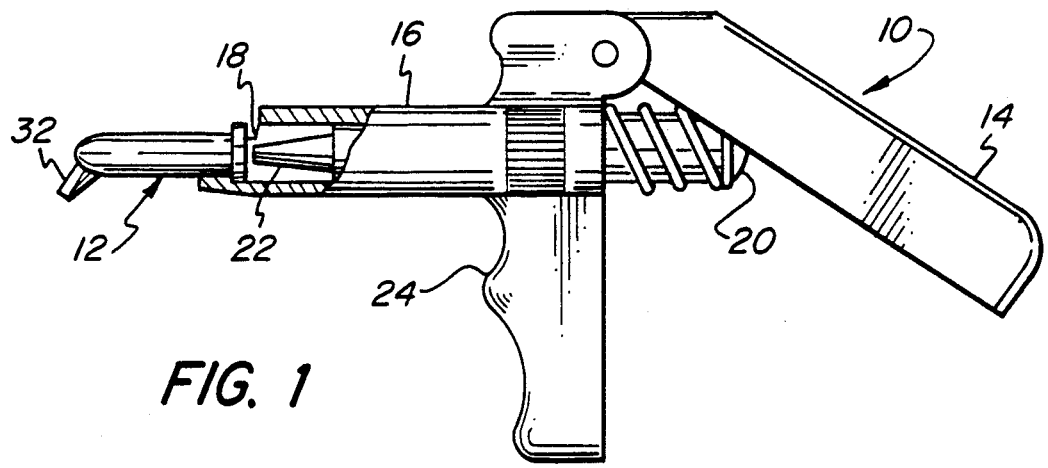
FIG. 1 is a partial sectional view illustrating the application o the present invention.

FIG. 1 illustrates a gun or syringe 10 for use with a tip or cartridge 12 of the present invention. The syringe 10 has a back handle 14 and a barrel 16 placed through a front handle 24. Within barrel 16 is a breach opening 18, through which cartridge 12 can be placed. Once cartridge 12 is placed through breach opening 18, the plunger 20 is advanced by back handle 14 so that plunger tip 22 forces the material contained within cartridge 12 out of the nozzle 32. A similar dental material application system is disclosed in U.S. Pat. No. 4,198,756 entitled "Manual Extruder" issuing to Dragan on Apr. 22, 1980, which is herein incorporated by reference.

Figure 2:
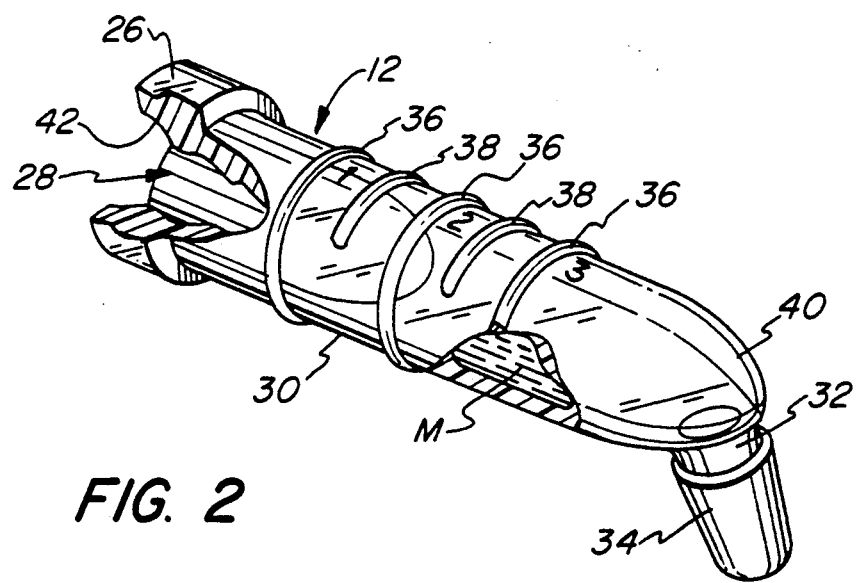
FIG. 2 is a partial section isometric view of one embodiment of the present invention.

FIG. 2 more clearly illustrates the present invention. FIG. 2 illustrates a cartridge 12 for holding a viscous dental material M similar to the device disclosed in U.S. Pat. No. 4,963,093 entitled "Dental Syringe Tip and Syringe Holder Therefor" issuing to Dragan on Oct. 16, 1990, which is herein incorporated by reference. However, the present invention illustrated in FIG. 2 is made of a material transparent to at least a portion of the visible light spectrum, and opaque to the actinic light of the dental material contained therein. Typically, the dental material contained within a dental cartridge of the type illustrated in FIG. 2 is light activated. Therefore, after the dental material is extruded from the cartridge 12, and exposed to light, the material will harden or cure. Therefore, prior to the present invention, all dental cartridges for containing light sensitive material were made of a substance opaque to all light. The cartridge 12 illustrated in FIG. 2, however, is made from a material not completely opaque to light, but is opaque, or will block the wavelength of light that is actinic to or that will activate or cure the dental material contained therein. This wavelength is typically about 480 nanometers and may range between 400-525 nanometers. Other wavelengths of light in the visible spectrum can be transmitted therethrough. Therefore, a dentist can visibly see the material contained within the cartridge 12, yet the light activated dental material will not cure even when the cartridge is exposed to light for relatively long periods of time.

The cartridge 12 can be made from a clear nylon or polypropylene using a transparent colorant having an orange tint. One transparent colorant that has been successfully used is CNYD13238, available from Reed Plastics Corp., Holden, Mass. This colorant has proven very successful in preventing curing of the dental material.

In FIG. 2, more specifically, the cartridge 12 comprises a rear flange 26 connected to a body or reservoir portion 30. The body portion 30 has an open end 42 and a closed discharge end 40. Communicating with the closed discharge end 40 is a discharge nozzle 32. Thereby, a two axes tip is formed. The first longitudinal axes is that of the body portion 30, and the second longitudinal axes is that of the discharge nozzle 32. These two axes typically intersect at an angle of approximately 135 degrees. This angle has been found to be most convenient in applying the dental material to teeth in the mouth and is often referred to as the "contra" angle. On the body portion 30 are placed dosing graduations or indicia 36 and partial dosing graduations or indicia 38. The dosing graduations 30 and 36 may be either raised, recessed, or painted on the body portion 30. These dosing graduations permit the dentist to individually load an empty cartridge 12 with a dental material of his choice in an amount required by a specific application. Therefore, essentially no dental material, which can be costly, is wasted. Alternatively, the cartridge 12 can be pre-loaded with varying amounts of dental material. In this way, the dentist can visibly see the quantity of dental material within the cartridge 12 and select the cartridge containing the appropriate volume of material needed for a specific patient. Therefore, a cartridge containing more material than needed in a particular application is not wasted due to the practice of not using the same cartridge 12 on more than one patient to prevent cross contamination.

In use, the dentist places dental material M in the open end 42 of cartridge 12. The dentist places the material in cartridge 12 until a desired dosing graduation is reached for the particular application. Thereby, the dentist can control the specific volume of material to be used. After obtaining the desired volume of material within cartridge 12, the dentist places a plug or piston 28 sealing the open end 22. At the same time, the dentist can place a nozzle cap 34 on the nozzle 32 thereby preventing any contamination or the entry of actinic light until such time as the cartridge 12 is to be used.

Figure 3:
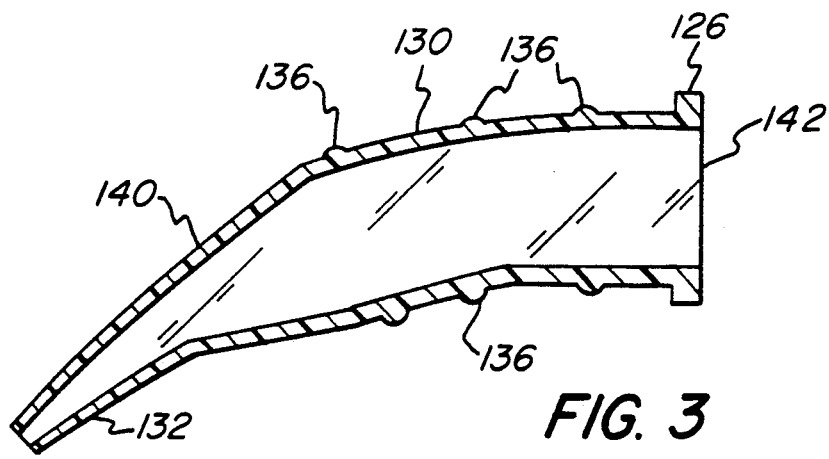
FIG. 3 is a cross section of another embodiment of the present invention.
Figure 4:
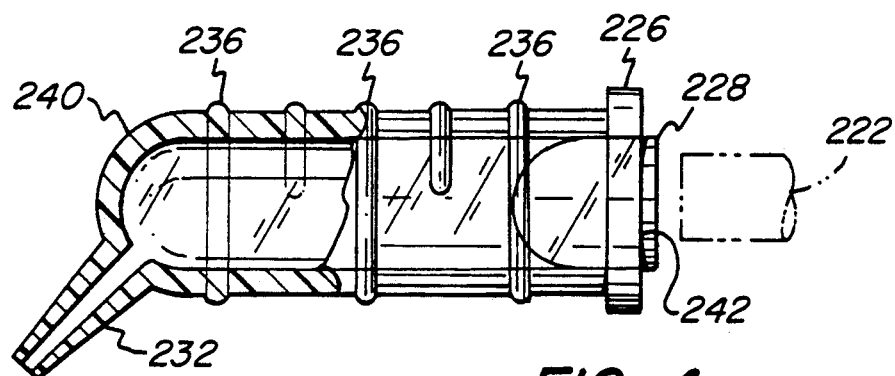
FIG. 4 is a partial sectional view of yet another embodiment of the present invention.
Figure 5:
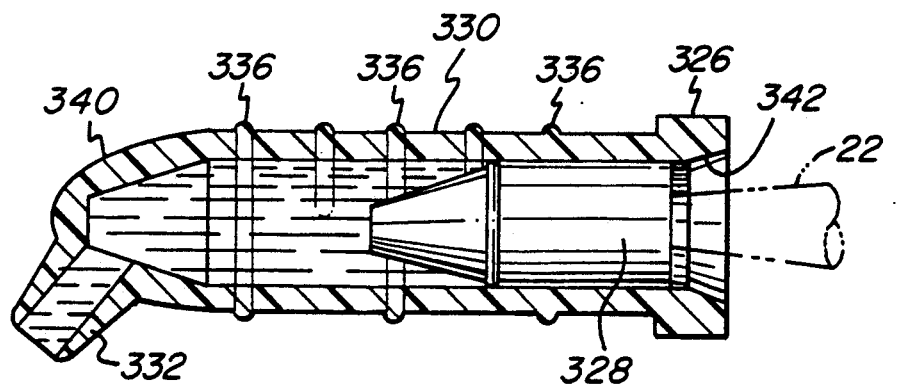
FIG. 5 is a longitudinal cross sectional view of yet a further embodiment of the present invention.

FIGS. 3-5 illustrate the various embodiments of a dental cartridge that can all be made of a material opaque to the actinic light of the dental material, but transparent to at least a portion of the visible light spectrum. FIG. 3 illustrates a relatively complex shape designed to improve visibility within the mouth of the cavity. The cartridge is comprised of a rear flange 126 connected to a body portion 130, a discharge end 140 and a discharge nozzle 132. On the body portion 130 are positioned dosing graduations 136.

FIG. 4 illustrates another dental cartridge configuration of the present invention. The cartridge illustrated in FIG. 4 is similarly made of a material opaque to the actinic light of the dental material contained therein, yet transparent to at least a portion of the visible light spectrum so that the dental material contained therein can be visibly seen. The cartridge illustrated in FIG. 4 comprises a rear flange 226 connected to a body portion 230. At either end of body portion 230 is an open end 242 and a closed discharge end 240. Adjacent closed discharge end 240 is a discharge nozzle 232. In this embodiment, the discharge end 240 is hemispherical. A piston 228 is illustrated in open end 242. The piston 242 is advanced by plunger tip 222 to extrude the material contained within the body portion 230. The piston 228 has a front surface that is of a shape that complements the closed discharge end 240. Body portion 230 has thereon dosing graduations or indicia 236.

FIG. 5 illustrates yet another cartridge configuration. This configuration comprises a flange 326 connected to a body portion 330 having an open end 342 and a discharge end 340. Adjacent discharge end 340 is a discharge nozzle 332. The discharge end 340 has an internal shape of a conical frustum or truncated cone. A piston 328 illustrated in the body portion 330 has a front end that complements the interior frusto-conical shape of the discharge end 340. Thereby, nearly all of the material contained within body portion 330 is extruded. However, a small portion of material left within the bore of the discharge nozzle 332 remains even when the piston 328 abuts the end of the discharge end 340. The piston 328 is advanced by plunger tip 22 illustrated in phantom. Body portion 330 has dosing graduations or indicia 336 thereon.

FIGS. 6-8 illustrate another embodiment of the invention that may be made of a completely opaque material, or of a material that is opaque to the actinic light of the dental material contained therein and transparent to at least a portion of the visible light spectrum. The cartridges illustrated in FIGS. 6-8 all have a toroidal segment body portion and a discharge nozzle having a common curved longitudinal axis.

The cartridge illustrated in FIG. 6 has a flange 426 attached to a toroidal segment body portion 430. Body portion 430 has an open end 442 and a discharge end 440. Adjacent the discharge end 440 is discharge nozzle 432. Discharge nozzle 432 is also a toroidal segment portion similar to that of body portion 430, however, nozzle 432 has a diameter smaller than that of body portion 430. Nozzle 432 and body portion 430 have a common curved longitudinal axis. Discharge end 440 has an interior shape that is frusto-conical. A modified piston 428 having an appendage 429 thereon can be used in combination with the cartridge illustrated in FIG. 6. The appendage 429 is adapted to fit within the nozzle portion 432 when the piston 428 is advanced to the discharge end 440. The nozzle 432 and the body portion 430 having a common curved axis, permits the appendage 429 to readily enter the nozzle 432 thereby extruding substantially all of the costly dental material contained within the cartridge. The appendage 429 can have a length from a portion of the length of the nozzle 432 to a length somewhat in excess of the length of nozzle 432. When the appendage length 429 is greater than that of the length of the nozzle 432, a portion of the appendage 429 will extend from the end of nozzle 432 when the piston 428 is completely advanced within the cartridge. This slight extension from the nozzle 432 of appendage 429 can be an indication that the material in the cartridge has been completely extruded, and that the cartridge is empty. This is most helpful when the cartridge body is completely opaque.

Nozzle 432 has a relief angle 444 at the end thereof. This relief angle 444 permits improved filling of a cavity. This relief angle permits the portion of the nozzle furthest away from the center of rotation to be longer than the portion of the nozzle 43 closest to the center of rotation of the body portion 430 and nozzle 432 toroidal segments.

FIG. 7 illustrates another cartridge having a flange 526 attached to a toroidal segment body portion 530. Body portion 530 has an open end 542 and a discharge end 540. Discharge end 540 is hemispherical in shape. Adjacent discharge end 540 is a toroidal segment nozzle 532. On body portion 530 are placed dosing graduations or indicia 536 and partial graduations or indicia 538. The piston 528 has a surface complementing the interior surface of the discharge end 540. Piston 528 also has an appendage 529 adapted to fit within the nozzle 532. Nozzle 532 also has a relief angle 544 improving the ability of the cartridge to fill a cavity.

FIG. 8 illustrates another cartridge and, additionally, show dashed lines that more specifically indicate the formation of the desired shape of the cartridge. The cartridge illustrated in FIG. 8 comprises a flange 626 attached to a toroidal segment body portion 630. Body portion 630 has an open end 642 and a discharge end 640. The discharge end 640, in this embodiment, is flat. Adjacent discharge end 640 and extending therefrom is a nozzle 632. Nozzle 632 has a longitudinal axis common with that of body portion 630. This common axis can clearly be seen to form part of a circumference C. This circumference C is created by a radius R pivoting at the central pivot point P. The toroidal segment is thereby formed having a mean radius R. The toroidal segment is a cylindrical toroidal segment, meaning that the interior diameter of the toroidal segment is circular and a constant. The angle formed between line A and line B is such that a tangent taken along the circumference at the intersection of line A and a tangent taken along the circumference at the intersection of line B will form an angle at their intersection of approximately 135 degrees. Therefore, the toroidal segment 630 will be less than approximately one-eighth of a whole toroid. Thereby, a convenient working angle of the nozzle portion is obtained with a single common curved longitudinal axis. This improves the visibility and the material flow within the cartridge over that of a more complex or two axes cartridge. This single common axes along a continuous smooth curve also permits the piston 628 to be guided easily in the interior bore of body portion 630. For long cartridges, the plunger tip 22 can be made to be slightly flexible permitting it to conform to the curve of the cartridge. Additionally, piston 628 can accommodate an appendage 629 that will be aligned within the bore of nozzle 632. This permits the complete extrusion of all the dental material contained within the cartridge, which has previously proven to be very difficult. This is especially important in applications where the dental material is costly.

The nozzle 632 also has a relief angle 644. Also, on body portion 630 is placed dosing graduations 636 and partial dosing graduations 638. These dosing graduations are helpful in providing the correct dose of dental material when the cartridge is made of a material that is transparent to visible light, yet opaque to the light actinic to the dental material. However, the cartridge can also be made completely opaque in the embodiments illustrated in FIGS. 6-8.

From the above, it can readily be appreciated that the present invention provides an improved dental cartridge that permits the dentist to select a dental material most appropriate for a particular application without being dependent upon the material supplier providing pre-filled single use cartridges. The dentist can simply use bulk material as conventionally supplied by the dental material supplier and insert the dental material from the bulk form into the dosing cartridge. The dentist, because the material within the cartridge is visible, can select the volume of material that is appropriate for the intended procedure. This saves considerable material and as a result lowers the cost of dental care to the patient. Additionally, the dentist can see the volume of material remaining in the cartridge so as not to start a procedure which may require more material than remains in the cartridge. This is especially important in obtaining a consistent filling. Additionally, the toroidal segment shape of several embodiments of the invention permits an appendage to be placed on the piston which permits the complete extrusion of all the dental material. The toroidal segment cartridge also improves visibility in the small confines of a patient's mouth.

Figure 9:
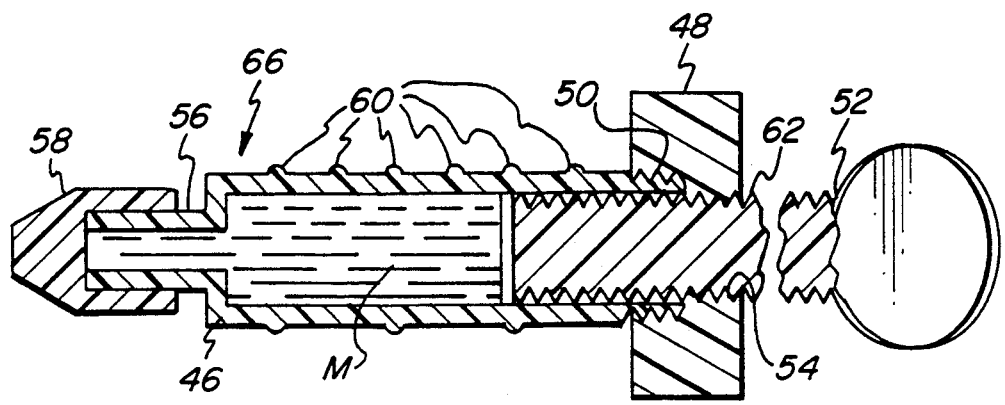
FIG. 9 is a cross section of another embodiment of the present invention.

FIG. 9 is yet another embodiment of the present invention. In FIG. 9, a bulk dental material cartridge is illustrated. The bulk cartridge contains a volume of material M sufficient for many applications to different patients. The bulk cartridge comprises a cylinder 46. Cylinder 46 is made of a material transparent to at least a portion of the visible light spectrum and opaque to the actinic light of the dental material. Therefore, dental material placed within cylinder portion 46 will be visible to the dentist, yet will not cure or set when exposed to light. At one end of the cylinder 46 is a threaded nut 48. Threaded nut 48 is placed over threads 50 on the cylinder 46. A threaded piston 52 has threads 62 thereon. The piston 52 is threaded into a bore in nut 48 having threads 54. At the other end of the cylinder 46 is a nozzle 56. Sealing nozzle 56 is a cap 58. Cap 58 can be made of the same material as cylinder 46 or of a completely opaque material so as to prevent light from entering the nozzle 56. Similarly, threaded piston 52 can be made of the same material as cylinder portion 46 or of a completely opaque material. Threaded piston 52 can also be made of a material having a contrasting color to that of cylinder portion 46 so that the end of the piston 52 can readily be seen within the cylinder 46. Additionally, on cylinder 46 are placed dosing lines 60. The dosing lines 60 provide units of measure for dispensing the dental material M. Because the cylinder 46 is transparent to visible light, the dentist, when dispensing the material, can visibly see the end of the piston 52. The end of the piston 52 can then be used, when matched with the dosing lines 60, to dispense a measured quantity of material M.

Figure 10:
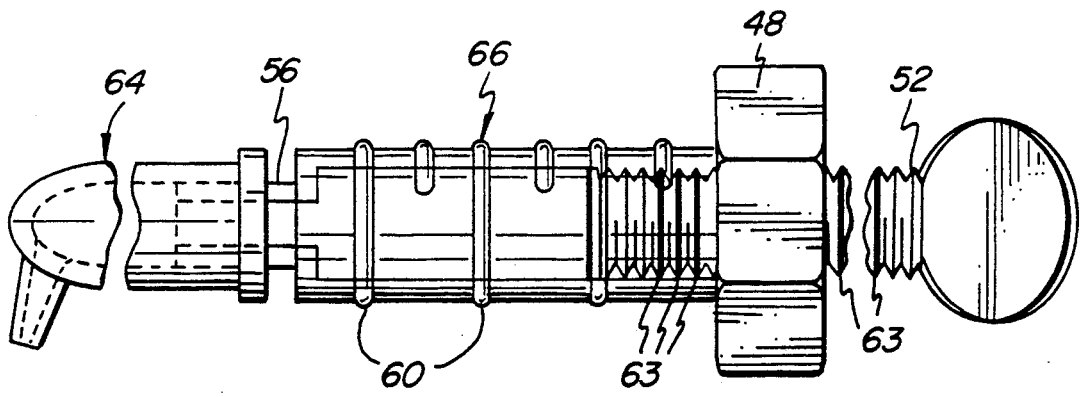
FIG. 10 is a front elevation view illustrating the application of the embodiment illustrated in FIG. 9.

FIG. 10 illustrates an application of the present invention embodied in bulk cartridge 66 and a single patient cartridge 64. The single patient cartridge 64 can be any one of those cartridges illustrated in FIGS. 2-8. The dentist can then place any one of the single patient cartridges generally represented as 64 in FIG. 10 onto the nozzle 56 of the bulk cartridge 66. Thereby, the dentist can advance threaded piston 52, dispensing the proper amount of material into the single patient cartridge 64. In this way, the dentist can easily load even completely opaque single patient cartridges 64 with the proper amount of material for a specific patient, depending upon the necessary work to be performed without wasting the expensive dental material. Additionally, this provides the dentist with a choice in his selection of materials without being dependent upon which materials the dental supply companies provide in the single patient cartridge form. Also illustrated in FIG. 10 are markings 63 placed on the threaded piston 52 to help indicate dosing. As the piston 52 is advanced displacing the material within the bulk cartridge 66 markings 63 can be used with reference to the surface of nut 48 to indicate the number of doses being placed in the patient cartridge 64. The markings 63 can be made of two alternating colors, or a pattern of more than two colors or shades of the same color indicating multiple doses. The markings 63 can be used with a bulk cartridge 66 that is transparent to visible light, or completely opaque. The markings 63 are most useful on a bulk cartridge that is completely opaque.

Although the preferred embodiment has been illustrated and described, it will be obvious to those skilled in the art that various modifications may be made without departing from the spirit and scope of this invention.

What is claimed is:

1. A dental cartridge used in dispensing light activated dental material comprising:
   a body portion having an open end and a discharge end, said body portion being made of a material transparent to at least a portion of the visible light spectrum and opaque to the actinic light of the dental material;
   a flange attached to the open end; and
   a nozzle attached to the discharge end;
   whereby the dentist can visually see the dental material contained in the cartridge while preventing hardening of the dental material contained therein.

2. A dental cartridge as in claim 1 further comprising: indicia on said body portion indicating dosing.

3. A dental cartridge as in claim 1 wherein: said flange, nozzle, and the discharge end are made of the same material.

4. A dental cartridge as in claim 1 wherein: the interior surface of said discharge end is hemispherical.

5. A dental cartridge as in claim 1 wherein: the interior surface of the discharge end is conical frustum shaped.

6. A dental cartridge as in claim 1 further comprising: a piston adapted to fit within said body portion.

7. A dental cartridge as in claim 6 wherein: said piston has a complementary shape to that of the discharge end.

8. A dental cartridge used in dispensing dental material comprising:
   a body portion formed from a toroidal segment having an open end and a discharge end, said body portion made of a material transparent to at least a portion of the visible light spectrum and opaque to the actinic light of the dental material;
   a flange attached to the open end; and
   a nozzle having a bore attached to the discharge end.

9. A dental cartridge as in claim 8 wherein: said body portion has a circular lateral cross section.

10. A dental cartridge as in claim 9 wherein: the toroidal segment is less than one-eighth of the whole toroid.

11. A dental cartridge as in claim 9 further comprising:
    a piston having a shaped end complementing the discharge end; and
    an appendage extending from the shaped end of said piston adapted to fit in the bore of said nozzle.

12. A dental cartridge as in claim 11 wherein: said appendage has a length sufficient to extend out of said nozzle when said piston abuts said discharge end.

13. A dental cartridge as in claim 11 wherein: said nozzle and said body portion have a common longitudinal axis.

14. A dental cartridge as in claim 13 wherein: the interior surface of the discharge end is hemispherical.

15. A dental cartridge as in claim 13 wherein: the interior surface of the discharge end has a conical frustum shape.

16. A dental cartridge as in claim 13 wherein: the interior surface of the discharge end is flat.

17. A dental cartridge as in claim 8 further comprising: indicia means, on said body portion, for indicating the volume of material contained therein.

18. A dental cartridge as in claim 8 wherein said nozzle is cut at a relief angle.

19. A dental dispensing cartridge comprising:
    a tubular body defining a reservoir, said tubular body being opened at one end thereof, and closed at the other end thereof, said tubular body formed of a transparent material which is impervious to actinic light,
a discharge nozzle disposed at said closed end and in communication with said reservoir,
a predetermined amount of light activated dental material dispensed in said reservoir, and
a displaceable piston sealing the open end of said body portion, whereby the displacement of said piston effects the evacuation of the material contained in said reservoir.

20. A dental dispensing cartridge as defined in claim 19 wherein said body having a central axis thereof defining an ark of a circle.

* * * * *